United States Patent
Schmitt et al.

(10) Patent No.: US 7,149,756 B1
(45) Date of Patent: Dec. 12, 2006

(54) SYSTEM AND METHOD FOR DETERMINING THE PROBABLE EXISTENCE OF DISEASE

(75) Inventors: Armand J. Schmitt, Santa Rosa, CA (US); Jeffrey Aguilere, Santa Rosa, CA (US)

(73) Assignee: Medoctor, Inc., Napa, CA (US)

( * ) Notice: Subject to any disclaimer, the term of this patent is extended or adjusted under 35 U.S.C. 154(b) by 481 days.

(21) Appl. No.: 10/275,315

(22) PCT Filed: Oct. 16, 2000

(86) PCT No.: PCT/US00/28610

§ 371 (c)(1), (2), (4) Date: Jul. 2, 2003

(87) PCT Pub. No.: WO01/85021

PCT Pub. Date: Nov. 15, 2001

Related U.S. Application Data

(60) Provisional application No. 60/202,732, filed on May 8, 2000.

(51) Int. Cl.
G06Q 10/00 (2006.01)
A61B 5/00 (2006.01)

(52) U.S. Cl. .................. 707/104.1; 705/3; 705/2; 600/300

(58) Field of Classification Search ............... 600/300, 600/493; 705/2, 3; 707/104.1, 1
See application file for complete search history.

(56) References Cited

U.S. PATENT DOCUMENTS

| | | | | |
|---|---|---|---|---|
| 5,660,183 A | * | 8/1997 | Chiang et al. | 600/508 |
| 5,778,882 A | * | 7/1998 | Raymond et al. | 600/513 |
| 5,935,060 A | * | 8/1999 | Iliff | 600/300 |
| 6,022,315 A | | 2/2000 | Iliff | |
| 2001/0032099 A1 | * | 10/2001 | Joao | 705/2 |

* cited by examiner

*Primary Examiner*—Sam Rimell
*Assistant Examiner*—Rezwanul Mahmood
(74) *Attorney, Agent, or Firm*—Foley & Lardner LLP; Jay P. Hendrickson

(57) ABSTRACT

A computer implemented and interactive system for obtaining a patient's symptoms and other indications of disease, which are utilized to determine the probable existence of disease. The program generates a series of inquiries which are displayed to a patient who is asked to identify the body part which the patient believes is causing a physical or mental problem. The system's program uses a database of diseases and related symptoms to generate questions. Based upon the patient's answer to each question, the program determines the probability that the patient has one of the diseases contained in the database. When the patient has completed answering all of the questions, the system's program generates a report of the probable existence diseases, including the patient's most probable disease.

10 Claims, 10 Drawing Sheets

Vitals

Degree of Pain
- Off & On
- Constant
- Worst-ever
- Severe
- Moderate
- Light

Temperature
- High
- Fever
- Normal
- Sub

Weight

Blood Pressure

QUESTION GENERATION TABLE

| QUESTION PHRASES | TEMPLATE CODES |
|---|---|
| DO OTHERS | 3 |
| DO YOU | 3 |
| DO YOU HAVE | 2 |
| DO YOU HAVE A | 3 |
| ARE YOU | 3 |
| IS YOUR | 1 |
| HAVE YOU | 2 |
| HAVE YOU A | 3 |
| ARE YOUR | 1 |
| DOES YOUR | 1 |
| WHAT IS YOUR | 3 |
| HOW OFTEN | 3 |
| IS IT | 3 |
| HAVE YOU HAD | 3 |

FIG. 7

PREDIAGNOSIS REPORT

I.      Diseases ("ICD")     Probabilities

_____             _____%

_____             _____%

_____             _____%

_____             _____%

II.      Recommended Lab Tests

III.     Recommended Specialists

IV.     Questions & Answers and Medical History

V.      Confirm Prediagnosis

Yes

SYSTEM AND METHOD FOR DETERMINING THE PROBABLE EXISTENCE OF DISEASE

The description which follows is for a system and method for determining the probable existence of disease.

TECHNICAL FIELD

The present invention generally relates to the use of database systems for the purpose of determining the probable existence of disease, and more specifically, to the use of such systems by health care providers to more efficiently and accurately determine the probable existence of disease.

BACKGROUND ART

The present health care system for processing patients from patient intake through physician diagnosis and treatment is well-known. Health care providers, such as hospitals, medical clinics or health maintenance organizations, provide a multi-step process involving the patient and several different health care professionals. Typically, the patient is initially directed by a receptionist to sign in, and if it is the patient's first visit to the health care provider, to complete a medical history questionnaire, including a description of the patient's symptoms, known drug interactions, and allergies. After waiting in a lobby or reception area for an indeterminate amount of time, the patient is usually next seen by a nurse or nurse practitioner who escorts the patient to a consultation or treatment room where the nurse takes and records the patient's vitals, usually his or her weight, temperature and blood pressure. The nurse will normally ask the patient about the patient's symptoms and records the patient's answers on a medical chart. At this point, the patient will normally be asked to wait in the consultation room until the patient's treating physician is able to see the patient.

Before seeing the patient, the physician will usually look at the nurse's notes on the patient's chart. During the physician's consultation with the patient, the doctor will again ask the patient to describe his or her symptoms, again writing the patient's answers on the chart. The physician will then normally conduct a physical examination of the patient and, ultimately, diagnose the patient's disease or condition. If the physician is unsure of the diagnosis, he or she may recommend that the patient see a specialist to make a diagnosis, and/or may order that certain laboratory tests be performed. Once the diagnosis is made, the physician prescribes a course of treatment or therapy.

There are several aspects of the above-described health care system which contribute to its deficiencies and limitations. For example, after the patient has checked in with the receptionist and possibly completed a medical questionnaire, the patient typically waits for several minutes before actually seeing a nurse. Naturally, during this waiting period, no information about the patient's current medical condition is being obtained. Further, the patient is repeatedly asked, by one or more nurses and ultimately by the treating physician, to describe his or her symptoms. Each time the health care practitioner records the patient's responses on the patient's chart. More thorough practitioners may also ask the patient to describe his or her personal and family medical histories, again maybe more than once. Obtaining information about the patient's personal and family medical histories in this fashion is rife with potential inaccuracies due to its reliance on the patient's memory.

Inaccuracies in a patient's personal and family medical histories may, in particular, lead to an incorrect diagnosis by the treating physician. An incorrect diagnosis may also result from the physician's inadvertent failure to consider the significance of the patient's symptoms to all possible diseases, especially those symptoms that indicate disease or condition about which the physician may not have much experience or familiarity. In this regard, a helpful diagnostic tool would be something that would prompt the physician to recommend that the patient see a specialist who had the requisite experience or to suggest to the treating physician that certain, possibly new, laboratory tests be carried out before a final diagnosis is made.

Accordingly, it is the purpose and goal of the present invention to overcome the inadequacies and limitations of the current health care system for processing patients from patient intake through physician diagnosis and treatment.

DISCLOSURE OF INVENTION

The present invention is a new and unique computer implemented and interactive system and method for obtaining a patient's symptoms, and other indications and predispositions for disease, which are then utilized to determine the probable existence of disease. The patient's symptoms and other information are inputted by a patient into the programmed computer system in response to computer inquiries that are generated by a program stored within the memory of the computer system. The patient accesses the computer system by using a computer input and display device, located at the facility of a health care provider, such as a hospital, medical clinic or Health Maintenance Organization.

Once the patient has gained access to the computer system, the system's program generates a series of inquiries which are displayed on the patient's display device. Initially the patient is asked to identify the Body Part which the patient believes is causing or is related to the patient's physical or mental problem. Next, the patient is prompted to input the patient's vitals: weight, temperature, and blood pressure. The patient is also asked to indicate the degree of pain, if any, being experienced. Once the patient has identified a Body Part, the system's program retrieves from a Disease/Symptom database all of the diseases and their related symptoms, indications, and predispositions which are related to the Body Part.

The Disease/Symptom database is created, in part, from a publicly available list of diseases which contains virtually all of the presently known human diseases, with each disease being identified by a unique alphanumeric code pursuant to the International Classification of Diseases ("ICD" code). The total number of persons who have been diagnosed with each disease is also tracked and continually updated as new diagnoses are confirmed. Creation of the Disease/Symptom database is generally completed by associating a numerical value for each disease equal to the number of times each disease has been found to exist in a patient (referred to herein as the "Disease Person Count"), and associating a list consisting of each physical symptom (e.g., pain), predisposition (e.g., heart disease) and other indications of disease (e.g., toxic exposure, low white cell count) (hereinafter individually referred to for convenience as a "Symptom," or collectively as "Symptoms") to each disease. Each Symptom associated to a specific disease is also assigned a numerical value (referred to herein as the "Symptom Person Count") equal to the Disease Person Count for that disease.

Lastly, each Symptom and its associated Person Symptom Count is associated to a predetermined Body Part.

After all Symptoms are identified as pertaining to a Body Part, the system's program selects the Symptom, out of the list of Symptoms associated to the Body Part, which has the highest probability of indicating a disease related to the Body Part selected by the patient. This probability is determined by the program by comparing the Symptom with the highest Symptom Person Count to the sum of all Symptom Person Counts for the Body Part. After the most probable Symptom is identified, the program generates a question which asks the patient, depending upon which Symptom has been identified, whether he/she has a certain physical symptom, whether he/she or anyone in his/her family has, or has ever had, a specific disease, and whether he/she has recently been exposed to a certain environmental condition. After the patient answers the question, the program updates the probability that the patient has one of the diseases contained in the entire Disease/Symptom database. The probable existence of each disease in the database is updated due to the fact that a condition, namely the existence or nonexistence of a Symptom, has been indicated by the patient.

If the patient responds to an inquiry by affirming that he/she has the Symptom, the system's program then uses Bayesian statistics to update or incrementally increase the probable existence of each diseases in the Disease/Symptom database which is indicated by the patient's symptom. On the other hand, if the patient does not have the Symptom, then the program updates the Disease/Symptom database by either incrementally increasing or decreasing the probable existence of each diseases which does not exhibit the Symptom. The program then compares the disease probability for each disease in the Disease/Symptom database to a predetermined threshold value, and for each disease having a probability equal to or greater than the threshold, its Symptoms are added to the list of Symptoms associated to the Body Part previously identified by the patient, assuming the symptoms are not already listed. After the probability of each disease is updated, the Symptom is removed from the Disease/Symptom database. The system's program then selects the Symptom from the list of Symptoms associated to the Body Part which has the highest patient Symptom count of all remaining Symptoms. Then, the program repeats the process of generating a patient question based upon the Symptom, updating the probable existence of each disease in the Disease/Symptom database, comparing the disease probabilities to the predetermined threshold value, and removing the Symptom from the database. This repetitive process continues until all of the Symptoms from the Disease/Symptom database, which were originally identified to the patient's Body Part, are removed from the database. The system's program next displays and ultimately generates a disease probability report or "pre-diagnosis" report in which the patient's most probable disease is identified, along with a next most probable disease and other less probable diseases. The pre-diagnosis report is then made available to the health care practitioners and to the patient's treating or primary care physician.

It is anticipated that the patient's nurse or other health care practitioner will review the pre-diagnosis report to determine whether the information inputted by the patient into the system is accurate and whether the patient has adequately responded to the computer generated interview questions which identify the patient's Symptoms. It is also anticipated that the pre-diagnosis report will then be given to the treating physician before he/she sees the patient. In this manner, the physician will be able to obtain a comprehensive medical history and present condition of the patient, and most importantly a pre-diagnosis report of the patient's most probable disease and other less probable diseases. After reviewing the report, the physician will have obtained comprehensive medical information about the patient and the patient's likely disease, and as a result, will be thoroughly prepared to personally examine the patient. Once the physician completes the examination, he/she will then be fully informed about the patient and the patient's medical condition, and will be thoroughly prepared to reach a diagnosis of the patient's disease or condition. If the physician's own diagnosis is the same as the diagnosis predicted in the pre-diagnosis report, the doctor will be extra confident that he or she has correctly diagnosed the patient's actual disease. If the physician's diagnosis is different from the pre-diagnosis, the physician may be prompted to advise the patient to obtain a second opinion. The pre-diagnosis report may also prompt the treating physician to consider other, less probable, diseases about which he/she may not be completely familiar. In such cases, the treating physician may want to recommend that the patient see a specialist to evaluate the patient before a final diagnosis is made.

Another important aspect of the present invention is its ability to continually improve the accuracy of the computer system's determination of the probable existence of disease. Each time the system diagnoses a disease, which is confirmed by the treating physician and/or a specialist to be the patient's actual disease, the disease and its associated Symptoms are added to the Disease/Symptom database. As a result, the more times the system is used to generate a pre-diagnosis, the more statistical information is obtained about the number of patients who have been diagnosed with a disease. As the quantity of statistical information increases, the reliability and accuracy of the determination of the probable existence of disease similarly increases.

BRIEF DESCRIPTION OF DRAWINGS

FIG. 7 is a table which identifies "Question Phrases" and "Template Codes" and illustrates their relationship.

FIG. 10 is a diagram of a pre-diagnosis report.

BEST MODE FOR CARRYING OUT THE INVENTION

Figure 1:
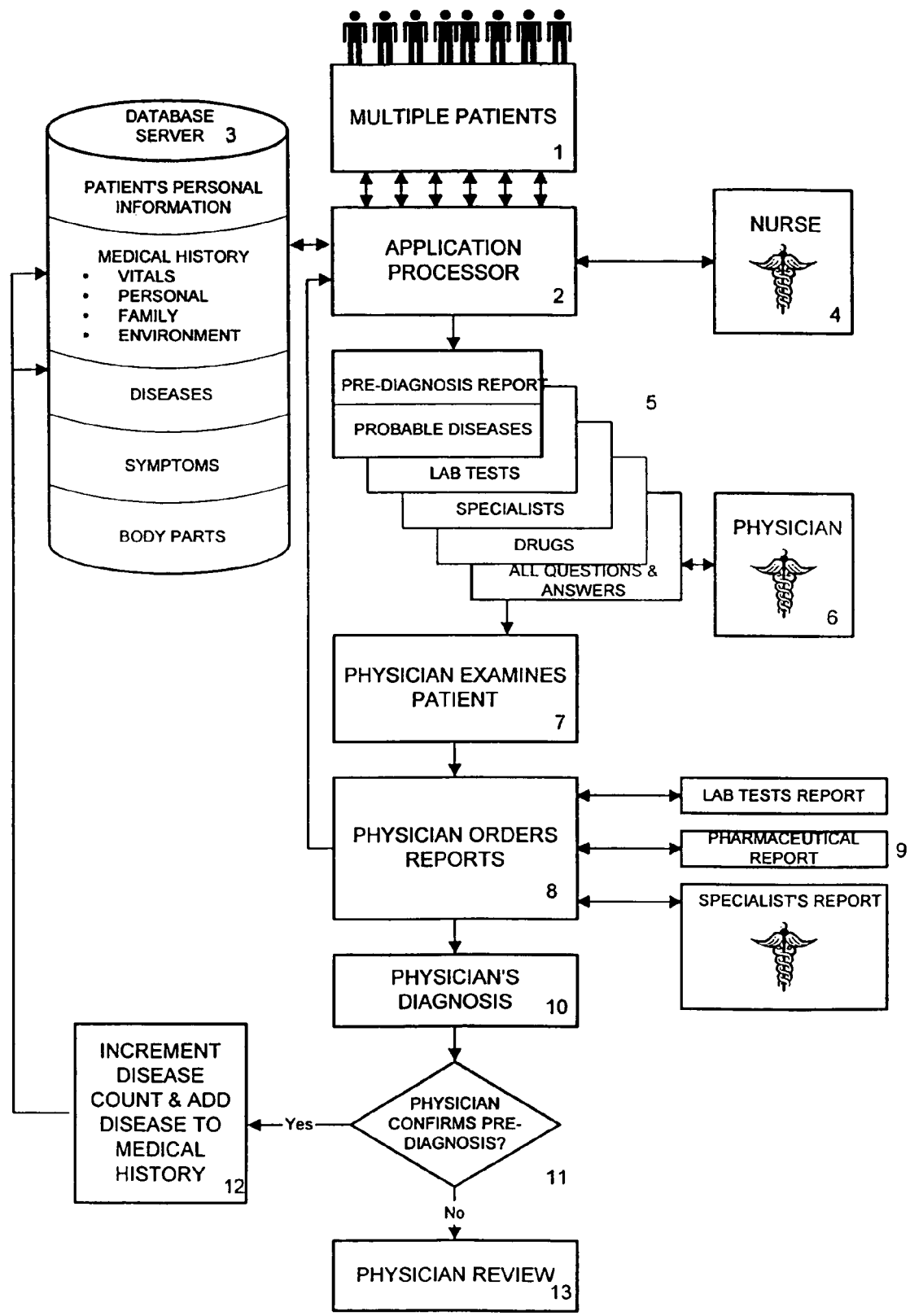
FIG. 1 is a block diagram and schematic which illustrates the overall architecture of the present invention

In a preferred embodiment of the present invention, the computer implemented and interactive system and method for determining the probable existence of disease is most readily utilized by a health care provider such as a hospital, medical clinic, or Health Maintenance Organization. In this regard, FIG. 1 illustrates the general architecture of the present invention which enables health care providers to process patients more efficiently and effectively during the patient intake phase, to more accurately and comprehensively obtain and record the patient's symptoms, and to assist the treating physician in reaching a correct diagnosis. Step 1 illustrates that the present invention allows the health care provider to simultaneously process a plurality patients, who are each connected, at step 2, to an application processor, comprising one or more programmed computer servers. The server may be programmed by using a program storage device, such as a CD-ROM, containing computer readable program code. An example of an acceptable CD-ROM is a Hewlett Packard CD-ROM, bearing model number hp 48x max IDE CD-ROM and product number D944A, having a storage capacity of 650 MB.

The patients are prompted by the application processor to input information relating to their medical condition and history and to answer processor generated questions indicating whether they have a specific Symptom which information is, in turn, stored at step 3 in the memory of a database server. The database server also stores the "Disease/Symptom" database containing lists of all diseases, all Symptoms, and all Body Parts. At step 4, a nurse or nurse practitioner reviews the medical information inputted by the patient and determines whether the patient has adequately responded to the questions about their Symptoms, and consults with the patient, if necessary, to correct any errors or inconsistent data. Once the patient's medical information has been verified, the programmed application processor uses the data stored in the database server to calculate the possible existence of all diseases. At step 5, a pre-diagnosis report is generated which identifies the patient's most probable disease and other less probable diseases. The report may also recommend that certain laboratory tests be performed, that a specialist be consulted, and that certain drugs be considered by the physician. And, at step 6, the pre-diagnosis report is presented to the physician, providing the doctor with an opportunity, before seeing the patient, to become thoroughly informed about the patient's medical condition and history and most importantly, informed about the patient's most probable disease and other less likely diseases which should be considered. At step 7, the patient's physician examines the patient and may make a preliminary diagnosis. At steps 8 and 9, the physician may order and receive a laboratory test report, a specialist's report and/or a pharmaceutical report. If a laboratory test is obtained which further describes the patient's physical condition (e.g., patient has a low white cell count), the processor also at step 8 prompts the physician to affirm that the condition exists and the processor recalculates the probable existence of all diseases and a revised pre-diagnosis report is generated. Finally, at step 10, the physician makes a final diagnosis based upon the information contained in the pre-diagnosis report, the doctor's examination, and upon any laboratory test results and/or the result of any specialist's report.

After the treating physician makes a final diagnosis, the physician is asked at step 11 to respond to an inquiry at the end of the pre-diagnosis report to either confirm that the pre-diagnosis was correct or to indicate that the pre-diagnosis was not correct. If the physician confirms that the pre-diagnosis correctly identified the patient's actual disease, the application processor updates the Disease/Symptom database at step 12 by incrementing the Patient Disease Count by one (1) and adding the disease to the patient's medical history stored in the database server. If the accuracy of the pre-diagnosis report is not confirmed, the physician at step 13 may further review the pre-diagnosis report, re-examine the patient, obtain additional laboratory tests, seek further analysis by a specialist and/or report to the health care provider of the inability to confirm the pre-diagnosis.

Figure 2:
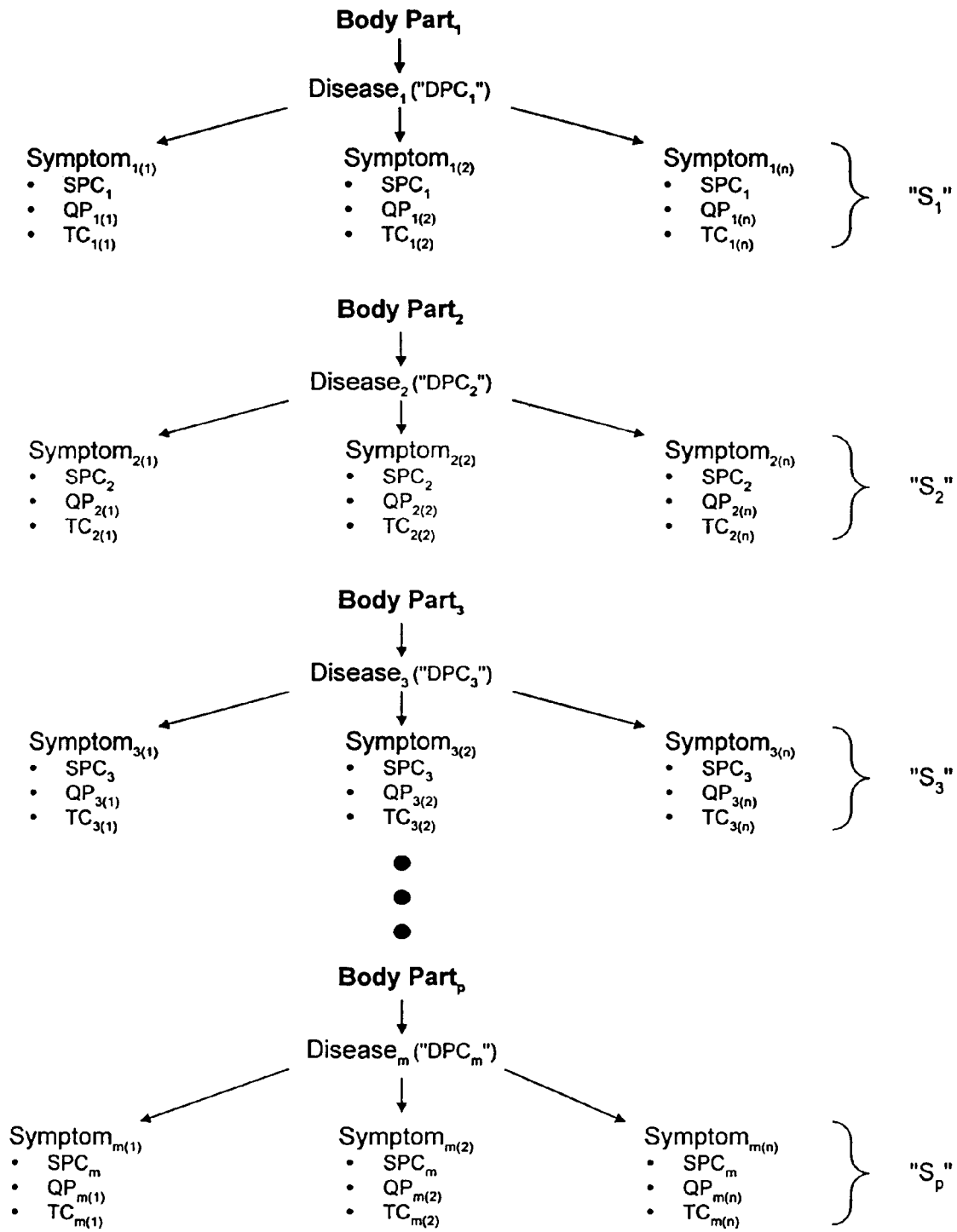
FIG. 2 is a schematic which illustrates the organizational structure of the Disease/Symptom database.
Figure 5:
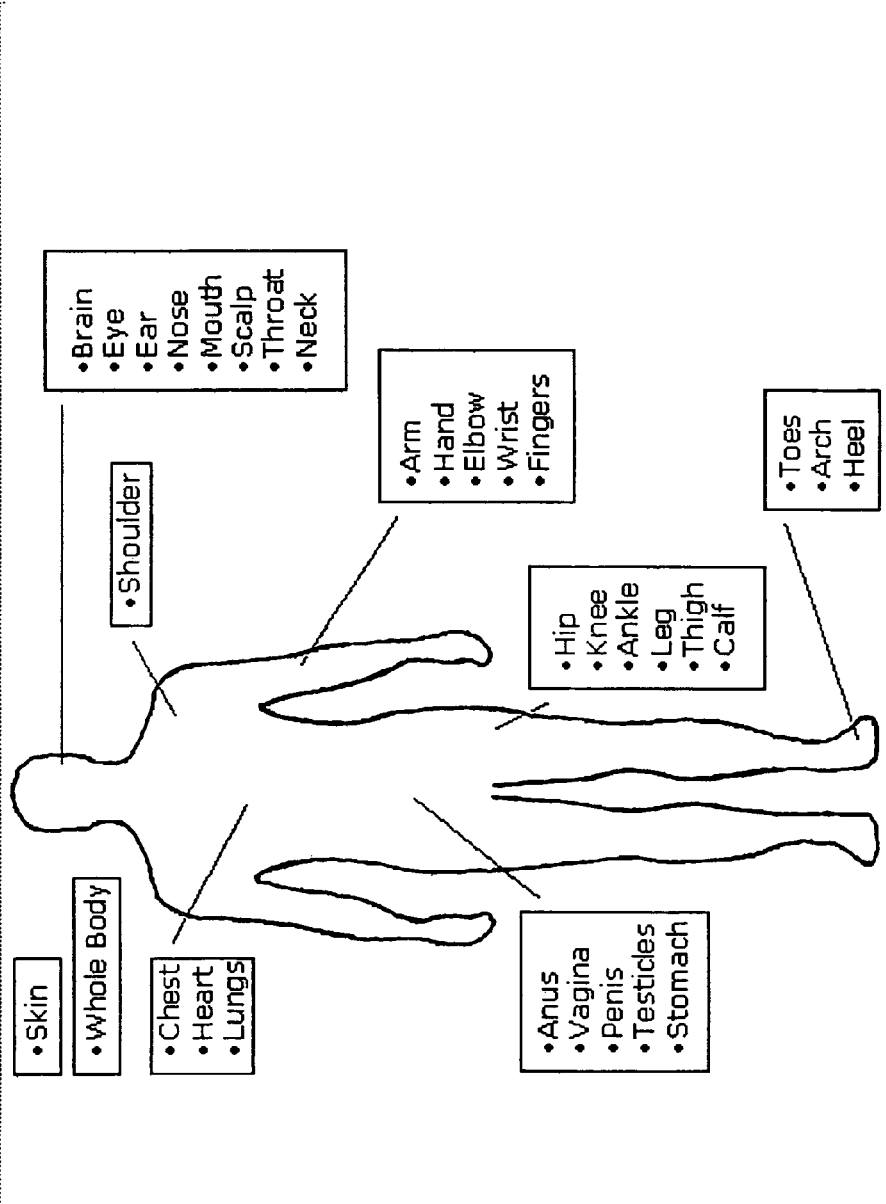
FIG. 5 is a diagram of a computer screen which the patient uses to identify a Body Part.

FIG. 2 generally illustrates the organizational structure and content of the Disease/Symptom database. Initially, the database identifies a predetermined number of human Body Parts, which are depicted in FIG. 2 as Body Part$_1$, Body Part$_2$, Body Part$_3$ . . . Body Part$_p$. The identity of each Body Part is as depicted in FIG. 5 and will be described further in connection with the subsequent description of that figure.

Next, the Disease/Symptom database associates with each Body Part virtually all the known diseases which are generally associated to that Body Part. The organization of each disease within the Disease/Symptoms database is shown in FIG. 2 as Disease$_1$, Disease$_2$, Disease$_3$ . . . Disease$_m$. Although the figure only illustrates a single disease in relation to a Body Part, it is likely that several diseases may be associated in the database to a given Body Part. In addition, each disease is associated with a "Disease Person Count" ("DPC"), illustrated in FIG. 2 as DPC$_1$, DPC$_2$, DPC$_3$ . . . DPC$_m$, which is a numerical value equal to the number of persons who have been confirmed to exhibit a specific disease. The identity of each disease is initially obtained from a publicly available list of diseases ("public database"), maintained and reported by the World Health Organization which contains virtually all of the presently-known human diseases. This public database assigns a unique, alphanumeric code to each disease pursuant to a scheme called the "International Classification of Diseases" ("ICD" code). Similarly, the present invention uses the ICD code to identify each disease in the Disease/Symptom database. The initial Disease Person Count of each disease has been obtained from other resources and publicly reported information which have confirmed that a certain number of persons exhibit each disease. This information has been compiled to establish a Disease Person Count for each disease in the Disease/Symptom database. This Disease Person Count information is also used to establish the initial probable existence of each disease by determining the quotient of the Disease Person Count for each disease divided by the total Disease Person Count for all diseases. In this manner, the present invention uses the World Health Organization public database and other publicly available information about the frequency of diseases to partially initialize the Disease/Symptom by providing a list of known diseases and a count of the number of persons who have exhibited each disease and the initial probable existence of each disease.

The Disease/Symptom database is further organized by associating with each disease a list of Symptoms which are known to indicate the disease or to predispose the patient to having the disease. In this regard, as discussed above in the Disclosure of Invention, "Symptoms" are defined herein to include the patient's physical symptoms (e.g., pain and stiffness), the patient's physical condition which is revealed by the physician's examination and/or laboratory tests (e.g., a heart murmur and a low white blood cell count), the patient's predisposition to disease (e.g., prior diseases of the patient and the patient's family), and environmental conditions which are known to be a factor in causing certain diseases. As further illustrated in FIG. 2, Disease$_1$ is associated with Symptom$_{1(1)}$, Symptom$_{1(2)}$ . . . Symptom$_{1(n)}$. In addition, the set of all Symptoms associated with each Body Part, is identified as set "S". More specifically, set S$_1$, S$_2$, S$_3$ . . . S$_p$ is each associated with Body Part$_1$, Body Part$_2$, Body Part$_3$ . . . Body Part$_p$, respectively. The Disease/Symptom database also associates with each Symptom a "Symptom Person Count" ("SPC") which is a numerical value equal to the Disease Person Count for the disease which is related to that Symptom and Body Part. For example, in FIG. 2, SPC$_1$ is the Symptom Person Count for Symptom$_{1(1)}$, Symptom$_{1(2)}$ . . . Symptom$_{1(n)}$, and SPC$_1$ equals DPC$_1$. As a result, the database is organized such that each Symptom Person Count is equal to the Disease Person Count for a given Body Part.

Lastly, the Disease/Symptom database associates with each Symptom a "Question Phase" ("QP") and a "Template Code" ("TC") which are used by the application processor to generate a question to be presented to the patient requesting that the patient indicate whether: 1) the patient has a physical symptom; 2) the patient has ever had a specific disease; 3) any member of the patient's family has had a specific disease; and 4) the patient has been exposed to an environmental condition.

Figure 3:
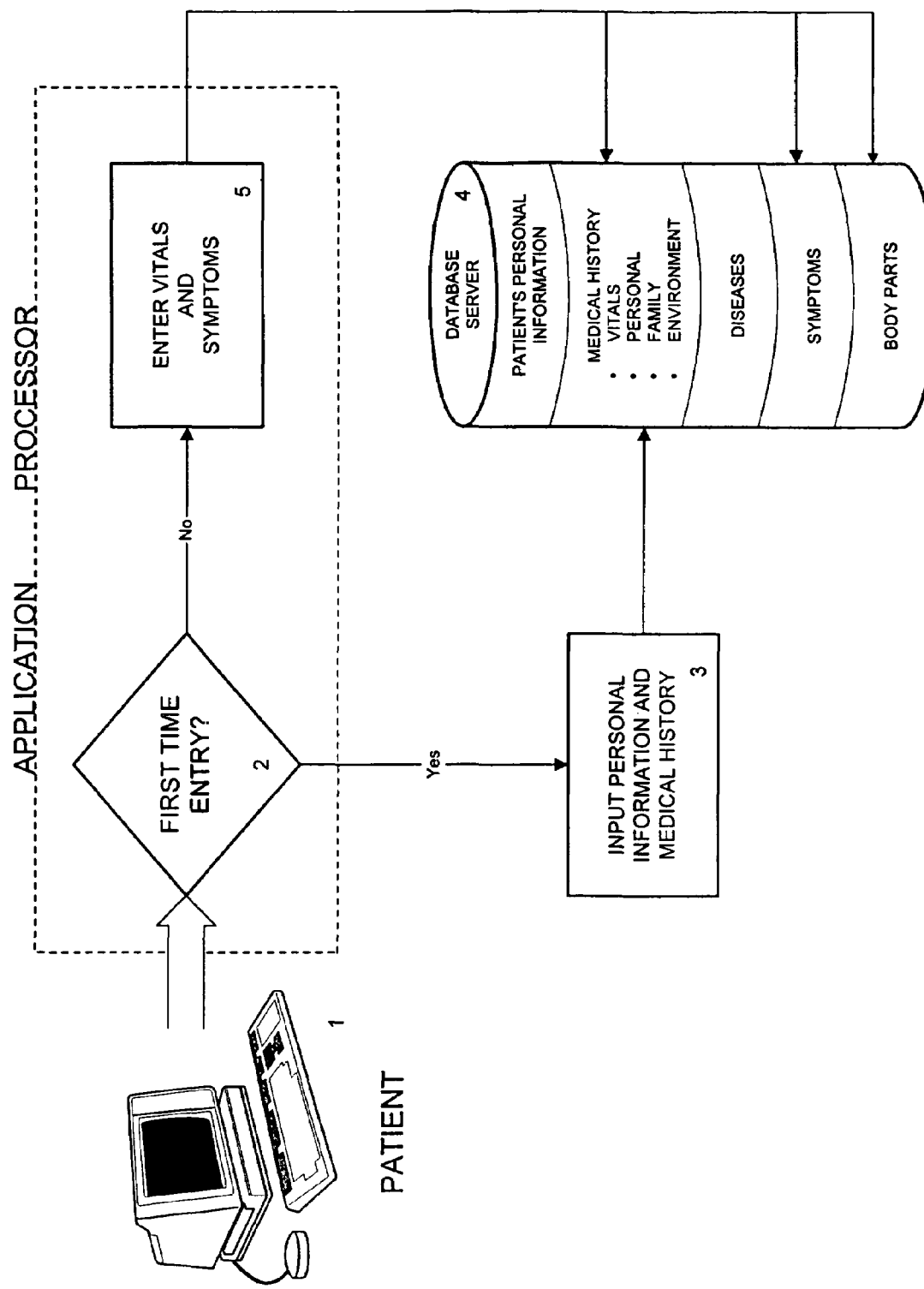
FIG. 3 is a block diagram and schematic which illustrates a patient's interaction with the application processor.

FIG. 3 illustrates in more detail the manner in which each patient enters his or her medical information using a computer monitor input and display device. Immediately, upon the patient's arrival at the health care provider's facility, he or she is directed to a private computer monitor area where the patient will be prompted by the system's application server to input his or her medical information. In a preferred embodiment, the patient's health care provider furnishes the patient with an identification card which the patient, as shown at step 1, swipes through a card reader connected to the application processor. If the processor determines that the patient is authorized, the patient's computer monitor is activated by the processor. Initially, at step 2, the processor determines whether the patient is entering medical data into the system for the first time. If the patient is a first time user, the processor prompts the patient at step 3 to enter their personal and family medical history by responding to questions presented to the patient on the monitor screen. Preferably, the monitor screen provides "touch-sensitive" radio button technology which allows the patient to respond to an inquiry by merely touching a radio button to indicate in the affirmative. Each time the patient indicates that he or she or a family member has had a certain disease, the processor at step 4 stores the disease in the database server as part of the patient's personal or family medical history. Similarly, if the patient identifies any recent environmental exposures, the information is stored in the database server.

Figure 4:
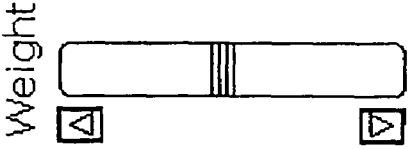
FIG. 4 is a diagram of a computer screen which the patient uses to input his or her vitals.
Figure 4:

After the patient has completed entering his or her medical history or if the patient is not a first time user, the application processor at step 5 prompts the patient to enter his or her vital information and personal symptoms. The processor displays a "Vitals" screen as illustrated in FIG. 4. One of the vitals displayed to the patient is a degree of pain indicator 1 and the patient is prompted to touch that portion of the display which corresponds to his or her level of pain. In the patient's private computer monitor area, each patient is also provided with sensory devices which the patient uses to obtain his or her temperature, weight and blood pressure. Once these values are obtained, the patient is again prompted to input each value into the system by touching the temperature display 2, weight display 3 and blood pressure display 4, and the Vitals are stored by the processor in the Disease/Symptom database. In another embodiment, each sensory device is connected to the processor which automatically stores the information in the Disease/Symptom database.

Once the patient has completed entering his or her Vitals, the processor displays on the patient's screen, as illustrated in FIG. 5, a human figure depicting a plurality of Body Parts, with each Body Part being further identified by a textual description and a radio button. This important aspect of the invention prompts the patient to identify that part (or parts) of his or her body which the patient believes is associated with the personal physical symptom or symptoms being experienced by the patient. After the patient identifies a Body Part by touching the radio button adjacent to said Body Part, the processor initiates another interactive process, as depicted in FIG. 6, in which the patient is asked a series of questions concerning the Symptoms related to the identified Body Part.

Figure 6:
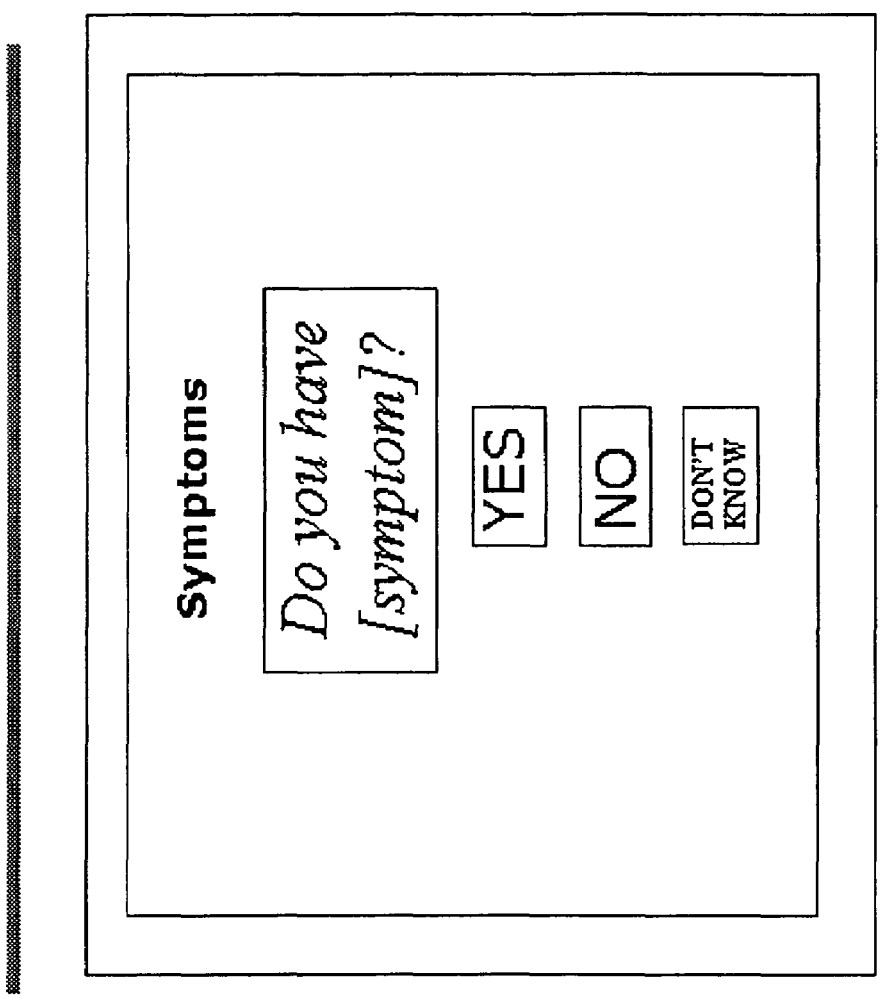
FIG. 6 is a diagram of a computer screen which the patient uses to indicate the existence or nonexistence of a Symptom.
Figure 8:
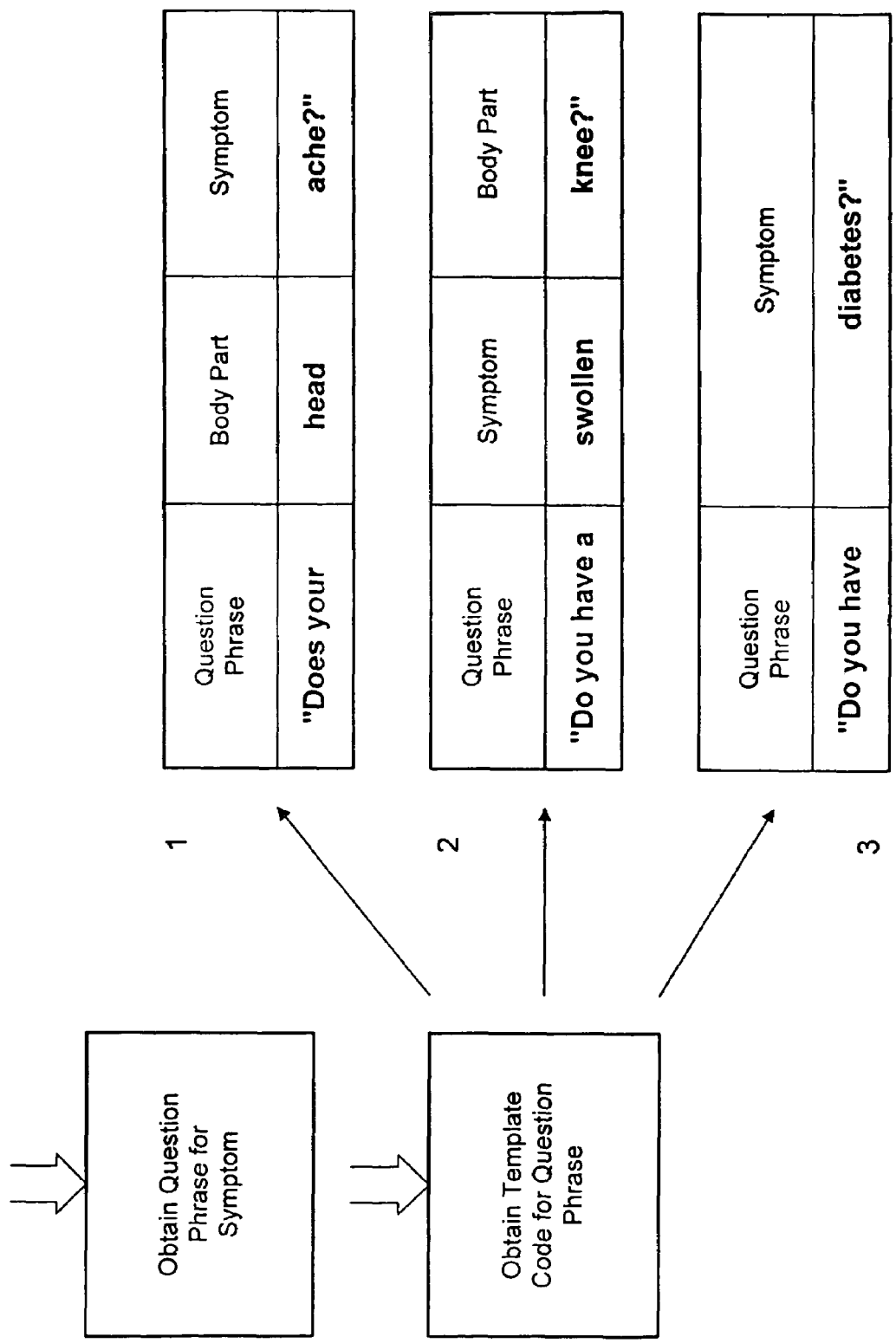
FIG. 8 is a block diagram and schematic which illustrates the manner in which the processor generates a question to be presented to the patient.

Before describing the patient's interaction with the system as illustrated in FIG. 6, FIGS. 7 and 8 are described in order to explain the manner in which the application processor generates each question which is presented to the patient. As shown in FIG. 7, the present invention also stores in the database server a table of "Question Phrases" and "Template Codes," either 1, 2, or 3, associated with each phrase. Further, each Questions Phrase ("QP") and its associated Template Code ("TC") is also associated to a specific Symptom stored in the "Disease/Symptom" database as described above and shown in FIG. 2.

The first step performed by the application processor in creating a question is to identify the Symptom out of the set of "S" Symptoms (i.e., all Symptoms related to the Body Part identified by the patient) which has the largest Symptom Person Count, which means that the Symptom has the highest frequency or total symptom numerical value out of all Symptoms in the set "S" related to a Body Part. Next, as shown in FIG. 8, the processor identifies the Question Phrase and Template Code associated with the identified Symptom. Based upon the Template Code identified, the processor selects either Template 1, 2, or 3. If Template 1 is selected, the sentence is constructed by beginning the sentence with the Question Phrase, placing the Body Part, previously identified by the patient, next, and the Symptom last (e.g., "Does your head ache"). If Template 2 is selected, the order of arrangement is Question Phrase, Symptom and Body Part (e.g., "Do you have a swollen knee"). And, if Template 3 is identified, the order is Question Phrase and Symptom (e.g., "Do you have diabetes"). Finally, the completed question is presented to the patient by the processor as shown in FIG. 6, and in a preferred embodiment the patient is prompted to respond by touching the screen to respond to the question by answering "YES," "NO" or "DON'T KNOW," indicating that: 1) he or she has or does not have the symptom or the disease; 2) that a family member has or has had the disease; or 3) he or she has or has not been exposed to an environmental condition.

Figure 9:
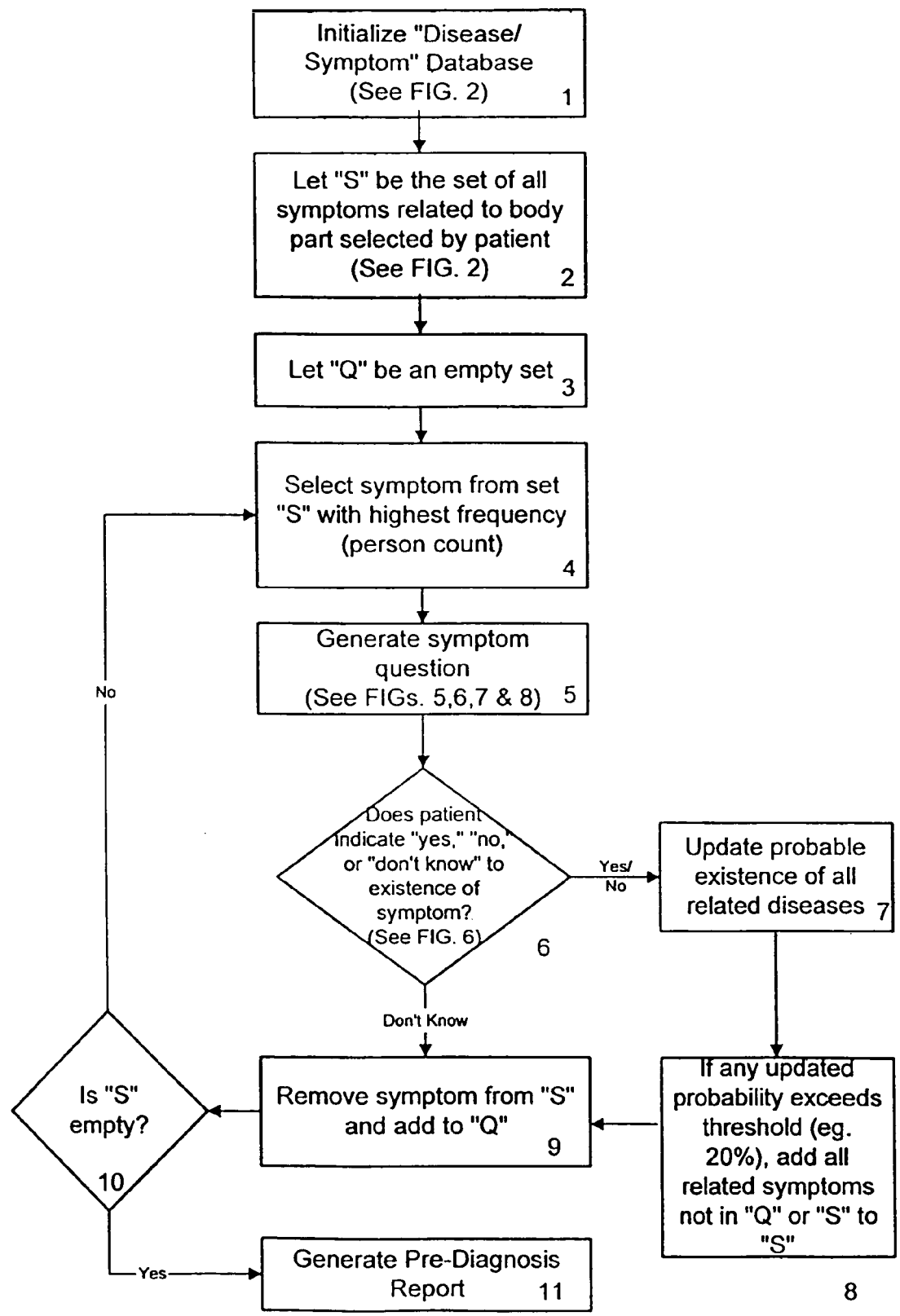
FIG. 9 is a flow chart which illustrates the manner in which the processor determines the probable existence of disease.

At this point the application processor utilizes the patient's answer, as illustrated in FIG. 9, to determine the probable existence of all diseases stored in the database server. In step 1 of FIG. 9, the processor initializes the Disease/Symptom database. This initialization process is the same as the process described above in connection with FIG. 2, in which the Disease/Symptom database is created by establishing a predetermined number of Body Parts, associating a list of diseases to each Body Part, associating a list of Symptoms to each disease, and establishing the initial probability of each disease in the database.

At step 2, the processor defines a set "S" to be all Symptoms related to a Body Part selected by the patient (see also FIG. 2), and at step 3, a empty set "Q" is defined. At step 4, the processor selects the Symptom out of all possible Symptoms ("S") identified in step 2 which has the highest frequency or Symptom Person Count (i.e. the total symptom numerical value) for the Body Part.

Once the Symptom with the highest Symptom Person Count has been identified, the processor at step 5 generates and displays a questions to the patient as described above in connection with FIGS. 5, 6, 7, and 8. If at step 6, the patient indicates by answering "YES" that he or she, or a family member, has or has had the Symptom (i.e., personal physical symptom or disease) or has been exposed to the Symptom (i.e., environmental condition), the processor proceeds to update or incrementally increase the probable existence of all diseases in the Disease/Symptom database which are indicated by the patient's Symptom. On the other hand, if the patient indicates that he or she does not have the Symptom by answering the question "NO," the processor updates the Disease/Symptom database by either incrementally increasing or decreasing the probable existence of each disease which is not indicated by the Symptom.

In either event, the probabilities are updated in accordance with Bayesian statistics:

$$Pr\{D|S\} = Pr\{D\}\frac{Pr\{S|D\}}{Pr\{S\}}$$

Where Pr {D|S} is the probability that disease D exists given the fact the patient has or does not have Symptom S; and Pr {D} is the probability that disease D exists without any condition.

When the patient indicates that he/she has a Symptom, Pr {S|D}/Pr {S} is equal to:

$$\frac{Pij}{Sj}$$

Where Pij is the conditional probability that Symptom j indicates disease i, and Sj is the unconditional probability of Symptom j.

Thus, for each disease i which is indicated by Symptom j, the probability of the disease is calculated as follows:

$$Pr_{(after)}\{Di\} = Pr_{(before)}\{Di\}\frac{Pij}{Sj}$$

$$\text{Where } Pij = \frac{\text{Symptom Person Count for Symptom } j}{\text{Total Symptom Person Count for Disease } i}$$

$$Sj = \frac{\text{Symptom Person Count for Symptom } j}{\text{Total Symptom Person Count for Symptom } j \text{ for all dieases } i}$$

If the patient indicates that he/she does not have the disease, Pr {S|D}/Pr {S} is determined as follows:

$$\frac{1 - Pij}{1 - Sj}$$

At step 8, the probable existence of all diseases is compared to a predetermined threshold value (e.g., a 20% probability) and for all diseases having a probability equal to or greater than the threshold, their Symptoms are added to the Disease/Symptom database if the database Symptoms are not already listed in set "S" or "Q." Then at step 9 the Symptom previously selected at step 4 is removed from the Disease/Symptom database since the existence or nonexistence of the Symptom has already been used to update all disease probabilities. At the same time, the Symptom and the fact of its existence or non-existence is added to data set "Q," which will be used later when the pre-diagnosis report is prepared, along with a listing of the patient's reported Symptoms.

Returning to step 6, if the patient does not respond to a question, the program proceeds directly to step 9 where the Symptom is removed from the Disease/Symptom database and added to "Q" as a Symptom about which the patient did not respond.

Continuing at step 10, the processor determines whether the Disease/Symptom database contains any more Symptoms. If it does, the program returns to step 4 and the process just described is repeated. When all Symptoms have been removed from the database, the program is complete, and the pre-diagnosis report is generated at step 11 and the report is displayed on a nurse display device and a physician display device.

The format of the pre-diagnosis report is illustrated in FIG. 10. In addition to identifying the patient's most probable disease and its "ICD" number, the report delineates the probable existence of all diseases which have met the predetermined threshold value. The report also sets forth any laboratory tests that are recommended based upon the identity of the most probable diseases. The pre-diagnosis report may also recommend that a specialist be consulted if the probability of the most probable disease and the next most probable disease or diseases is within a certain predetermined percentage (e.g., 5%). The report further contains a description of the patient's medical history and the patient's family history, and a listing of all questions presented to the patient with each response. If the physician orders laboratory tests and the test results further describe the patient's physical condition, which the present invention treats as another Symptom, the processor prompts the physician to indicate that the condition exists. Once the physician does so by using a physician data entry device such as a touch sensitive screen in connection with the processor, the processor recalculates the probable existence of all diseases based upon the fact another Symptom was found to exist, and generates and displays to the physician a revised pre-diagnosis report.

Finally, the pre-diagnosis report asks the physician to confirm the pre-diagnosis. In a preferred embodiment, confirmation of a pre-diagnosis shall also include all diseases which are determined to have a 95% or greater probability. If the physician confirms, based upon his or her own physical examinations and study of any laboratory test results, that the pre-diagnosis report correctly identified the most probable disease as the actual disease, or that one of the diseases identified by the report as part of a sublist of diseases having at least a 95% probability of existence, was the actual disease, the processor prompts the doctor to so indicate by using the physician's touch screen to answer "YES" that the pre-diagnosis is confirmed and, as illustrated in FIG. 1, the processor increases the Disease Person Count by one (1), and adds the disease to the patient's medical history. If the doctor is unable to confirm the pre-diagnosis, the physician may want to consider advising the patient to obtain a diagnosis from another physician and/or obtain further laboratory tests and/or additional evaluation from a specialist.

Although the present invention has disclosed as its preferred embodiment the circumstance in which patients input their medical information and Symptoms using a data entry method, such as a touch screen and sensory devices, located at the health care provider's facility, it will be readily understood by those skilled in the art that the present invention includes another embodiment in which patients' may enter their medical information and Symptoms from a remote location, such as their home, which is connected over a network to the application processor located at the health care facility. The data entry method at the remote location may consist of any type of data entry device, such as a monitor and keyboard or a touch screen. And, the network may include a proprietary intranet or the public internet. It must also be understood, however, that in this embodiment, after the patient has inputted his or her medical information, the patient will have to visit the health care provider in order to have a treating physician review the patient's pre-diagnosis report and make a final diagnosis.

Further, it should be apparent that many modifications may be made to the present invention without departing from the essential teachings of the invention. Accordingly, it will be understood by those skilled in the art that, within the scope of the appended claims, the invention may be practiced in embodiments other than those specifically described in this application.

INDUSTRIAL APPLICABILITY

The present invention has numerous advantageous industrial applications. Health care costs constitute a significant portion of every country's economy, and those costs are continuing to rise dramatically as the world population continues to grow. In addition, person's who can afford to have health insurance are experiencing significant increases in their insurance premiums.

Health care providers are no longer able to efficiently and effectively process patients from patient intake through physician diagnosis and treatment. Although the Health Maintenance Organization ("HMO") was originally developed to reduce the costs of treatment and insurance, in general, patients have become disenchanted with the HMO's slow and inefficient services. More seriously, patient's are noticing that administrators are increasingly preventing patients from obtaining proper medical care.

The present invention constitutes a significant advantage in the manner in which HMO's and all health care providers process patients. The present invention provides health care providers with the ability to simultaneously process multiple patients and to obtain their vital information without requiring the assistance of a nurse or other health care practitioners. The patient's medical information is stored in a computer database which constitutes a permanent and readily obtained record of each patient. The invention also provides a feature which automatically updates the patient's medical records as further information about the patient's medical condition becomes known. Efficiency is further increased because the patient's current symptoms are obtained electronically and automatically displayed to the patient's nurse and physician. Most significantly, the system of the present invention generates a pre-diagnosis report of the patient's condition or disease before he or she ever sees a doctor. The doctor's efficiency is enhanced because he or she is able to review the pre-diagnosis report to become thoroughly familiar with the patient's condition and the patient's possible diseases that should be considered during the patient's examination.

Another significant aspect of the present invention is that the more the invention is used the more valuable and accurate it becomes. Each time a physician confirms the existence of a disease which was predicted in the pre-diagnosis report, the doctor updates the invention's database of diseases which increases the probable existence of the disease. As the quantity of statistical information increases, the reliability and accuracy of the invention's determination of the probable existence of disease similarly increases.

We claim:
1. A method for determining the probable existence of disease comprising:
  a) providing a plurality of patient Body Parts;
  b) associating with each Body Part a list of diseases, and as to each disease in the list of diseases, associating a list of Symptoms which indicate said disease;
  c) associating with each disease in each list of diseases a disease numerical value equal to the number of persons who have been confirmed to exhibit said each disease;
  d) associating with each Symptom in each list of Symptoms, which indicate a specific disease, a symptom numerical value equal to the disease numerical value of said specific disease;
  e) calculating an initial probable existence of each disease in each list of diseases by determining the quotient of the disease numerical value of each disease divided by the sum of all disease numerical values for all diseases;
  f) calculating a total symptom numerical value for all identical Symptoms in all lists of Symptoms;
  g) identifying a set of Symptoms, and each Symptom's associated total symptom numerical value, which comprise all Symptoms associated to each Body Part;
  h) prompting a patient to identify a target Body Part which the patient associates to his or her physical or mental condition;
  i) identifying a target Symptom from the set of Symptoms associated to the target Body Part which has the highest total symptom numerical value;
  j) generating a question presented to the patient which asks the patient if the target Symptom is indicated or is not indicated;
  k) prompting the patient to respond to the question;
  l) updating the probable existence of each disease in each list of diseases based upon the patient's answer in accordance with the following formula:

$$Pr\{D|S\} = Pr\{D\} \frac{Pr\{S|D\}}{Pr\{S\}}$$

where D is a disease and S is a Symptom;
  m) identifying a qualifying disease in each list of diseases with a probability greater than a predetermined threshold value, and adding each Symptom associated to said qualifying disease to the set of Symptoms associated to the target Body Part if the Symptom to be added is not already in the set;
  n) deleting the target Symptom from the set of Symptoms associated to the target Body Part;
  o) repeating steps i through n above until each Symptom contained in the set of Symptoms associated to the Body Part is deleted; and
  p) generating a list of diseases and the probable existence of each disease in the list, including the identity of a most probable disease having the highest probability of existence.
2. The method as in claim 1 in which the step of generating a question further includes assembling the question from a list of possible question phrases and a template code associated to each question phrase, whereby the syntax of the sentence is determined by the Body Part identified by the patient and the Symptom with the highest total symptom numerical value.

3. A method for determining the probable existence of disease comprising:
   a) providing a plurality of patient Body Parts;
   b) associating with each Body Part a list of diseases, and as to each disease in the list of diseases, associating a list of Symptoms which indicate said disease;
   c) associating with each disease in each list of diseases a disease numerical value equal to the number of persons who have been confirmed to exhibit said each disease;
   d) associating with each Symptom in each list of Symptoms, which indicate a specific disease, a numerical Symptom value equal to the disease numerical value of said specific disease;
   e) calculating an initial probable existence of each disease in each list of diseases by determining the quotient of the disease numerical value of each disease divided by the sum of all disease numerical values for all diseases;
   f) calculating a total symptom numerical value for all identical Symptoms in all lists of Symptoms;
   g) identifying a set of Symptoms, and each Symptom's associated total symptom numerical value, which comprise all Symptoms associated to each Body Part;
   h) prompting a patient to identify a target Body Part which the patient associates to his or her physical or mental condition;
   i) identifying a target Symptom from the set of Symptoms associated to the target Body Part which has the highest total symptom numerical value;
   j) generating a question presented to the patient which asks the patient if the target Symptom is indicated or is not indicated;
   k) prompting the patient to respond to the question;
   l) updating the probable existence of each disease in each list of diseases based upon the patient's answer in accordance with the following formula:

$$Pr\{D|S\} = Pr\{D\}\frac{Pr\{S|D\}}{Pr\{S\}}$$

where D is a disease and S is a Symptom;
   m) identifying a qualifying disease in each list of diseases with a probability greater than a predetermined threshold value, and adding each Symptom associated to said qualifying disease to the set of Symptoms associated to the target Body Part if the Symptom to be added is not already in the set;
   n) deleting the target Symptom from the set of Symptoms associated to the target Body Part;
   o) repeating steps i through n above until each Symptom contained in the set of Symptoms associated to the Body Part is deleted;
   p) generating a list of diseases and the probable existence of each disease in the list, including the identity of a most probable disease having the highest probability of existence; and
   q) updating the probable existence of the most probable disease by incrementing the disease numerical value of said most probable disease by one (1) if the patient's actual disease is determined to be the most probable disease.

4. A method for determining the probable existence of disease comprising:
   a) providing a plurality of patient Body Parts;
   b) associating with each Body Part a list of diseases, and as to each disease in the list of diseases, associating a list of Symptoms which indicate said disease;
   c) associating with each disease in each list of diseases a disease numerical value equal to the number of persons who have been confirmed to exhibit said each disease;
   d) associating with each Symptom in each list of Symptoms, which indicate a specific disease, a symptom numerical value equal to the disease numerical value of said specific disease;
   e) calculating an initial probable existence of each disease in each list of diseases by determining the quotient of the disease numerical value of each disease divided by the sum of all disease numerical values for all diseases;
   f) calculating a total symptom numerical value for all identical Symptoms in all lists of Symptoms;
   g) identifying a set of Symptoms, and each Symptom's associated total symptom numerical value, which comprise all Symptoms associated to each Body Part;
   h) prompting a patient to identify a target Body Part which the patient associates to his or her physical or mental condition;
   i) identifying a target Symptom from the set of Symptoms associated to the target Body Part which has the highest total symptom numerical value;
   j) generating a question presented to the patient which asks the patient if the target Symptom is indicated or is not indicated;
   k) prompting the patient to respond to the question;
   l) updating the probable existence of each disease in each list of diseases based upon the patient's answer in accordance with the following formula:

$$Pr\{D|S\} = Pr\{D\}\frac{Pr\{S|D\}}{Pr\{S\}}$$

where D is a disease and S is a Symptom;
   m) identifying a qualifying disease in each list of diseases with a probability greater than a predetermined threshold value, and adding each Symptom associated to said qualifying disease to the set of Symptoms associated to the target Body Part if the Symptom to be added is not already in the set;
   n) deleting the target Symptom from the set of Symptoms associated to the target Body Part;
   o) repeating steps i through n above until each Symptom contained in the set of Symptoms associated to the Body Part is deleted;
   p) generating a list of diseases and the probable existence of each disease in the list, including the identity of a sublist containing each probable disease having a probability of existence in excess of a predetermined amount; and
   q) updating the probable existence of a single probable disease in the sublist by incrementing the disease numerical value of said single probable disease by one (1) if the patient's actual disease is determined to be the single probable disease.

5. An interactive computer system comprising:
   a) a programmed computer processor;
   b) a database server having a memory, said database server in electronic communication with the processor;

c) a plurality of patient data input and display devices all in electronic communication with the processor;
d) prompting a patient, out of a plurality of patients, to enter his or her vitals into the memory of a database server by using one of said patient data entry devices in communication with the processor and to similarly enter the patient's personal medical history, family medical history and exposure to environmental conditions into the database server;
e) storing a list of Body Parts in the memory of the database server;
f) storing in said memory a list of diseases associated with each Body Part, and as to each disease in the list of diseases, storing a list of Symptoms which indicate each said disease;
g) storing in said memory a disease numerical value associated with each disease in each list of diseases, said disease numerical value having a value equal to the number of persons who have been confirmed to exhibit said each disease;
h) storing in said memory a symptom numerical value associated with each Symptom in each list of Symptoms, which indicate a specific disease, said symptom numerical value having a value equal to the disease numerical value of said specific disease;
i) identifying with the processor a set of Symptoms, and each Symptom's associated symptom numerical value, which comprise all Symptoms associated to each Body Part;
j) calculating an initial probable existence of each disease in each list of diseases by using the processor to determine the quotient of the disease numerical value of each disease divided by the sum of all disease numerical values for all diseases and storing the results in the memory of the database server;
k) calculating a total symptom numerical value for all identical Symptoms in each list of Symptoms by using the processor to determine the sum of all symptom numerical values for all identical Symptoms in each list, and storing the results in the memory of the database server;
l) displaying to the patient on one of said patient display devices a human figure having a plurality of Body Parts;
m) prompting the patient to identify, using the patient data entry device, a target Body Part, out of all Body Parts displayed, which the patient believes is associated to his or her physical or mental condition;
n) identifying with the processor a target Symptom from the set of Symptoms associated to the target Body Part which has the highest total symptom numerical value and generating a question presented to the patient on the patient display device which asks the patient if the target Symptom is or is not indicated;
o) prompting the patient to respond to the question using the patient data entry device;
p) updating the probable existence of each disease in each list of diseases based upon the patient's answer by using the processor to determine said probable existence in accordance with the following formula:

$$Pr\{D|S\} = Pr\{D\}\frac{Pr\{S|D\}}{Pr\{S\}}$$

where D is a disease and S is a Symptom;
q) identifying with the processor a qualifying disease in each list of diseases with a probability greater than a predetermined threshold value, adding each Symptom associated to said qualifying disease to the set of Symptoms associated to the target Body Part if the Symptom to be added is not already in the set, and deleting the target Symptom from the set of Symptoms associated to the target Body Part;
r) repeating steps n through q above until each Symptom contained in the set of Symptoms associated to the Body Part is deleted;
s) generating a pre-diagnosis report by using the processor to identify a list of diseases and the probable existence of each disease in the list, including the identity of a most probable disease having the highest probability of existence;
t) displaying the pre-diagnosis report to a patient's nurse on a nurse display device whereby the nurse may review the patient's vitals, medical history, environmental exposures and Symptoms to determine whether the information inputted by the patient is accurate and whether the patient has adequately responded to the computer generated interview questions which identify the patient's Symptoms;
u) displaying the pre-diagnosis report to a patient's physician on a physician display device whereby the physician may review the report to obtain medical information about the patient and the patient's condition, including information about the probable existence of diseases related to the patient's medical information and condition;
v) prompting the patient's physician to confirm, by using a physician data entry device in communication with the processor, that the doctor's own diagnosis of the patient's actual disease is the same as the most probable disease described in the pre-diagnosis report; and
w) updating the probable existence of the most probable disease by using the processor to increment the disease numerical value of said most probable disease by one (1) if the patient's physician confirms that the most probable disease is his or her actual disease.

6. An interactive computer system comprising:
a) a programmed computer processor;
b) a database server having a memory, said database server in electronic communication with the processor;
c) a plurality of patient data input and display devices all in electronic communication with the processor;
d) prompting a patient, out of a plurality of patients, to enter his or her vitals into the memory of a database server by using one of said patient data entry devices in communication with the processor and to similarly enter the patient's personal medical history, family medical history and exposure to environmental conditions into the database server;
e) storing a list of Body Parts in the memory of the database server;
f) storing in said memory a list of diseases associated with each Body Part, and as to each disease in the list of diseases, storing a list of Symptoms which indicate each said disease;
g) storing in said memory a disease numerical value associated with each disease in each list of diseases, said disease numerical value having a value equal to the number of persons who have been confirmed to exhibit said each disease;
h) storing in said memory a symptom numerical value associated with each Symptom in each list of Symptoms, which indicate a specific disease, said symptom numerical value having a value equal to the disease numerical value of said specific disease;

i) identifying with the processor a set of Symptoms, and each Symptom's associated symptom numerical value, which comprise all Symptoms associated to each Body Part;

j) calculating an initial probable existence of each disease in each list of diseases by using the processor to determine the quotient of the disease numerical value of each disease divided by the sum of all disease numerical values for all diseases and storing the results in the memory of the database server;

k) calculating a total symptom numerical value for all identical Symptoms in each list of Symptoms by using the processor to determine the sum of all symptom numerical values for all identical Symptoms in each list, and storing the results in the memory of the database server;

l) displaying to the patient on one of said patient display devices a human figure having a plurality of Body Parts;

m) prompting the patient to identify, using the patient data entry device, a target Body Part, out of all Body Parts displayed, which the patient believes is associated to his or her physical or mental condition;

n) identifying with the processor a target Symptom from the set of Symptoms associated to the target Body Part which has the highest total symptom numerical value and generating a question presented to the patient on the patient display device which asks the patient if the target Symptom is or is not indicated;

o) prompting the patient to respond to the question using the patient data entry device;

p) updating the probable existence of each disease in each list of diseases based upon the patient's answer by using the processor to determine said probable existence in accordance with the following formula:

$$Pr\{D|S\} = Pr\{D\}\frac{Pr\{S|D\}}{Pr\{S\}}$$

where D is a disease and S is a Symptom;

q) identifying with the processor a qualifying disease in each list of diseases with a probability greater than a predetermined threshold value, adding each Symptom associated to said qualifying disease to the set of Symptoms associated to the target Body Part if the Symptom to be added is not already in the set, and deleting the target Symptom from the set of Symptoms associated to the target Body Part;

r) repeating steps n through q above until each Symptom contained in the set of Symptoms associated to the Body Part is deleted;

s) generating a pre-diagnosis report for by using the processor to identify a list of diseases and the probable existence of each disease in the list, including the identity of each probable disease having a probability of existence in excess of a predetermined amount;

t) displaying the pre-diagnosis report to a patient's nurse on a nurse display device whereby the nurse may review the patient's vitals, medical history, environmental exposures and Symptoms to determine whether the information inputted by the patient is accurate and whether the patient has adequately responded to the computer generated interview questions which identify the patient's Symptoms;

u) displaying the pre-diagnosis report to a patient's physician on a physician display device whereby the physician may review the report to obtain medical information about the patient and the patient's condition, including information about the probable existence of diseases related to the patient's medical information and condition;

v) prompting the patient's physician to confirm by using the physician data entry device in communicating with the processor, that the doctor's own diagnosis of the patient's actual disease is the same as one of the probable diseases; and w) updating the probable existence of said one probable disease by using the processor to increment the disease numerical value of said one probable disease by one (1) if the patient's physician confirms that the probable disease is his or her actual disease.

7. An interactive computer system comprising:

a) a programmed computer processor;

b) a database server having a memory, said database server in electronic communication with the processor;

c) a plurality of patient data input and display devices all in electronic communication with the processor;

d) prompting a patient, out of a plurality of patients, to enter his or her vitals into the memory of a database server by using one of said patient data entry devices in communication with the processor and to similarly enter the patient's personal medical history, family medical history and exposure to environmental conditions into the database server;

e) storing a list of Body Parts in the memory of the database server;

f) storing in said memory a list of diseases associated with each Body Part, and as to each disease in the list of diseases, storing a list of Symptoms which indicate each said disease;

g) storing in said memory a disease numerical value associated with each disease in each list of diseases, said disease numerical value having a value equal to the number of persons who have been confirmed to exhibit said each disease;

h) storing in said memory a symptom numerical value associated with each Symptom in each list of Symptoms, which indicate a specific disease, said symptom numerical value having a value equal to the disease numerical value of said specific disease;

i) identifying with the processor a set of Symptoms, and each Symptom's associated symptom numerical value, which comprises all Symptoms associated to each Body Part;

j) calculating an initial probable existence of each disease in each list of diseases by using the processor to determine the quotient of the disease numerical value of each disease divided by the sum of all disease numerical values for all diseases and storing the results in the memory of the database server;

k) calculating a total symptom numerical value for all identical Symptoms in each list of Symptoms by using the processor to determine the sum of all symptom numerical values for all identical Symptoms in each list, and storing the results in the memory of the database server;

l) displaying to the patient on one of said patient display devices a human figure having a plurality of Body Parts;

m) prompting the patient to identify, using the patient data entry device, a target Body Part, out of all Body Parts displayed, which the patient believes is associated to his or her physical or mental condition;

n) identifying with the processor a target Symptom from the set of Symptoms associated to the target Body Part which has the highest total symptom numerical value and generating a question presented to the patient on the patient display device which asks the patient if the target Symptom is or is not indicated;

o) prompting the patient to respond to the question using the patient data entry device;

p) updating the probable existence of each disease in each list of diseases based upon the patient's answer by using the processor to determine said probable existence in accordance with the following formula:

$$Pr\{D|S\} = Pr\{D\}\frac{Pr\{S|D\}}{Pr\{S\}}$$

where D is a disease and S is a Symptom;

q) identifying with the processor a qualifying disease in each list of diseases with a probability greater than a predetermined threshold value, adding each Symptom associated to said qualifying disease to the set of Symptoms associated to the target Body Part if the Symptom to be added is not already in the set, and deleting the target Symptom from the set of Symptoms associated to the target Body Part;

r) repeating steps n through q above until each Symptom contained in the set of Symptoms associated to the Body Part is deleted;

s) generating a pre-diagnosis report by using the processor to identify a list of diseases and the probable existence of each disease in the list;

t) displaying the pre-diagnosis report to a patient's nurse on a nurse display device whereby the nurse may review the patient's vitals, medical history, environmental exposures and Symptoms to determine whether the information inputted by the patient is accurate and whether the patient has adequately responded to the computer generated interview questions which identify the patient's Symptoms;

u) displaying the pre-diagnosis report to a patient's physician on a physician display device whereby the physician may review the report to obtain medical information about the patient and the patient's condition, including information about the probable existence of diseases related to the patient's medical information and condition;

v) prompting the physician to indicate, by using a the physician data entry device in communication with the processor, that the patent exhibits a condition revealed in laboratory tests;

w) updating the probable existence of each disease in each list of diseases based upon the physician's indication that the condition exists in accordance with the following formula:

$$Pr\{D|S\} = Pr\{D\}\frac{Pr\{S|D\}}{Pr\{S\}}$$

where D is a disease and S is a Symptom;

x) generating a revised pre-diagnosis report for the physician including a list of diseases and a revised probable existence of each disease in the list, including the identify of a most probable disease having the highest probability of existence;

y) prompting the patient's physician to confirm, by using the physician data entry device in communication with the processor, that the doctor's own diagnosis of the patient's actual disease is the same as the most probable disease described in the revised pre-diagnosis report; and z) updating the probable existence of the most probable disease by using the processor to increment the disease numerical value of said most probable disease by one (1) if the patient's physician confirms that the most probable disease is his or her actual disease.

8. An interactive computer system comprising:

a) a programmed computer processor;

b) a database server having a memory, said database server in electronic communication with the processor;

c) a plurality of patient data input and display devices all in electronic communication with the processor;

d) prompting a patient, out of a plurality of patients, to enter his or her vitals into the memory of a database server by using one of said patient data entry devices in communication with the processor and to similarly enter the patient's personal medical history, family medical history and exposure to environmental conditions into the database server;

e) storing a list of Body Parts in the memory of the database server;

f) storing in said memory a list of diseases associated with each Body Part, and as to each disease in the list of diseases, storing a list of Symptoms which indicate each said disease;

g) storing in said memory a disease numerical value associated with each disease in each list of diseases, said disease numerical value having a value equal to the number of persons who have been confirmed to exhibit said disease;

h) storing in said memory a symptom numerical value associated with each Symptom in each list of Symptoms, which indicate a specific disease, said symptom numerical value having a value equal to the disease numerical value of said specific disease;

i) identifying with the processor a set of Symptoms, and each Symptom's associated symptom numerical value, which comprises all Symptoms associated to each Body Part;

j) calculating an initial probable existence of each disease in each list of diseases by using the processor to determine the quotient of the disease numerical value of each disease divided by the sum of all disease numerical values for all diseases and storing the results in the memory of the database server;

k) calculating a total symptom numerical value for all identical Symptoms in each list of Symptoms by using the processor to determine the sum of all symptom numerical values for all identical Symptoms in each list, and storing the results in the memory of the database server;

l) displaying to the patient on one of said patient display devices a human figure having a plurality of Body Parts;

m) prompting the patient to identify, using the patient data entry device, a target Body Part, out of all Body Parts displayed, which the patient believes is associated to his or her physical or mental condition;

n) identifying with the processor a target Symptom from the set of Symptoms associated to the target Body Part which has the highest total symptom numerical value and generating a question presented to the patient on the patient display device which asks the patient if the target Symptom is or is not indicated;

o) prompting the patient to respond to the question using the patient data entry device;

p) updating the probable existence of each disease in each list of diseases based upon the patient's answer by using the processor to determine said probable existence in accordance with the following formula:

$$Pr\{D|S\} = Pr\{D\}\frac{Pr\{S|D\}}{Pr\{S\}}$$

where D is a disease and S is a Symptom;

q) identifying with the processor a qualifying disease in each list of diseases with a probability greater than a predetermined threshold value, adding each Symptom associated to said qualifying disease to the set of Symptoms associated to the target Body Part if the Symptom to be added is not already in the set, and deleting the target Symptom from the set of Symptoms associated to the target Body Part;

r) repeating steps n through q above until each Symptom contained in the set of Symptoms associated to the Body Part is deleted;

s) generating a pre-diagnosis report by using the processor to identify a list of diseases and the probable existence of each disease in the list;

t) displaying the pre-diagnosis report to a patient's nurse on a nurse display device whereby the nurse may review the patient's vitals, medical history, environmental exposures and Symptoms to determine whether the information inputted by the patient is accurate and whether the patient has adequately responded to the computer generated interview questions which identify the patient's Symptoms;

u) displaying the pre-diagnosis report to a patient's physician on a physician display device whereby the physician may review the report to obtain medical information about the patient and the patient's condition, including information about the probable existence of diseases related to the patient's medical information and condition;

v) prompting the physician to indicate, by using a physician data entry device in communication with the processor, that the patient exhibits a condition revealed in laboratory tests;

w) updating the probable existence of each disease in each list of diseases based upon the physician's indication that the condition exists in accordance with the following formula:

$$Pr\{D|S\} = Pr\{D\}\frac{Pr\{S|D\}}{Pr\{S\}}$$

where D is a disease and S is a Symptom;

x) generating a revised pre-diagnosis report for the physician including a list of diseases and a revised probable existence of each disease in the list, including the identity of each probable disease having a probability of existence in excess of a predetermined amount;

y) prompting the physician to confirm, by using the physician data entry devise, in communication with the processor, that the doctor's own diagnosis of the patient's actual disease is the same as one of the probable diseases described in the revised pre-diagnosis report; and z) updating the probable existence of said one probable disease by using the processor to increment the disease numerical value of said one probable disease by one (1) if the patient's physician confirms that the probable disease is his or her actual disease.

9. A program storage device readable by a computer, tangibly embodying a program of instructions executable by the computer to perform method steps for determining the probable existence of disease, said method steps comprising:

a) providing a plurality of patient Body Parts;

b) associating with each Body Part a list of diseases, and as to each disease in the list of diseases, associating a list of Symptoms which indicate said disease;

c) associating with each disease in each list of diseases a disease numerical value equal to the number of persons who have been confirmed to exhibit said each disease;

d) associating with each Symptom in each list of Symptoms, which indicate a specific disease, a symptom numerical value equal to the numerical value of said specific disease;

e) calculating an initial probable existence of each disease in each list of diseases by determining the quotient of the disease numerical value of each disease divided by the sum of all disease numerical values for all diseases;

f) calculating a total symptom numerical value for all identical Symptoms in all lists of Symptoms;

g) identifying a set of Symptoms, and each Symptom's associated total numerical value, which comprises all Symptoms associated to each Body Part;

h) prompting a patient to identify a target Body Part which the patient associates to his or her physical or mental condition;

i) identifying a target Symptom from the set of Symptoms associated to the target Body Part which has the highest total numerical value;

j) generating a question presented to the patient which asks the patient if the target Symptom is indicated or is not indicated;

k) prompting the patient to respond to the question;

l) updating the probable existence of each disease in each list of diseases based upon the patient's answer in accordance with the following formula:

$$Pr\{D|S\} = Pr\{D\}\frac{Pr\{S|D\}}{Pr\{S\}}$$

where D is a disease and S is a Symptom;

m) identifying a qualifying disease in each list of diseases with a probability greater than a predetermined threshold value, and adding each Symptom associated to said qualifying disease to the set of Symptoms associated to the target Body Part if the Symptom to be added is not already in the set;

n) deleting the target Symptom from the set of Symptoms associated to the target Body Part;

o) repeating steps i through n above until each Symptom contained in the set of Symptoms associated to the Body Part is deleted; and p) generating a list of diseases and the probable existence of each disease in the list, including the identity of a most probable disease having the highest probability of existence.

10. A computer program product for use with a pre-diagnosis report generator, said computer program product comprising:
   a) computer readable program code for prompting a patient to enter his or her vitals into the memory of a database server by using a patient data entry device in communication with the processor and similarly prompting the patient to enter the patient's medical history, family medical history and exposure to environmental conditions into the database server;
   b) computer readable program code for accessing a list of Body Parts stored in the memory of the database server;
   c) computer readable program code for causing the list of Body Parts to be displayed to the patient on a patient display device;
   d) computer readable program code for accessing in the memory of the database server a list of diseases associated with each Body Part, and as to each disease in the list of diseases, accessing a list of Symptoms, associated to each disease, which indicate said disease;
   e) computer readable program code for accessing in said memory a disease numerical value associated with each disease in each list of diseases, said disease numerical value having a value equal to the number persons who have been confirmed to exhibit said disease;
   f) computer readable program code for accessing in said memory a symptom numerical value associated with each Symptom in each list of Symptoms which indicate a specific disease, said symptom numerical value having a value equal to the disease numerical value of said disease;
   g) computer readable program code for identifying a set of Symptoms, and each Symptom's associated symptom numerical value, which comprise all Symptoms associated to each Body Part;
   h) computer readable program code for calculating an initial probable existence of each disease in each list of diseases by determining the quotient of the disease numerical value of each disease divided by the sum of all disease numerical values for all diseases and storing the results in the memory of the database server;
   i) computer readable program code for calculating a total symptom numerical value for all identical Symptoms in all lists of Symptoms and to storing the results in the memory of the database server;
   j) computer readable program code for displaying to the patient on the patient display device a human figure having a plurality of Body Parts;
   k) computer readable program code for prompting the patient to identify, using the patient data entry device, a target Body Part, out of all Body Parts displayed, which the patient believes is associated to his or her physical or mental condition;
   l) computer readable program code for identifying a target Symptom from the set of Symptoms associated to the target Body Part which has the highest total symptom numerical value and generating a question presented to the patient on the patient display device which asks the patient if the target Symptom is or is not indicated;
   m) computer readable program code for prompting the patient to respond to the question using the patient data entry device;
   n) computer readable program code for updating the probable existence of each disease in each list of diseases based upon the patient's answer in accordance with the following formula:

$$Pr\{D|S\} = Pr\{D\}\frac{Pr\{S|D\}}{Pr\{S\}}$$

where D is a disease and S is a Symptom;
   o) computer readable program code for identifying a qualifying disease in each list of diseases with a probability greater than a predetermined threshold value, adding each Symptom associated to said qualifying disease to the set of Symptoms associated to the target Body Part if the Symptom to be added is not already in the set, and deleting the target Symptom from the set of Symptom associated to the target Body Part;
   p) computer readable program code for repeating steps l through o above until each Symptom contained in the set of Symptoms associated to the Body Part is deleted;
   q) computer readable program code for generating a pre-diagnosis report including a list of diseases and the probable existence of each disease in the list, including the identity of a most probable disease having the highest probability of existence;
   r) computer readable program code for displaying the pre-diagnosis report to a patient's nurse on a nurse display device whereby the nurse may review the patient's vitals, medical history, environmental exposures and Symptoms to determine whether the information inputted by the patient is accurate and whether the patient has adequately responded to the computer generated interview questions which identify the patient's Symptoms;
   s) computer readable program code for displaying the pre-diagnosis report to a patient's physician on a physician display device whereby the physician may review the report to obtain medical information about the patient and the patient's condition, including information about the probable existence of diseases related to the patient's medical information and condition;
   t) computer readable program code for prompting the patient's physician to confirm, by using the physician's data entry device in communication with the processor, that the doctor's own diagnosis of the patient's actual disease is the same as the most probable disease described in the pre-diagnosis report; and
   u) computer readable program code for updating the probable existence of the most probable disease by incrementing the numerical value of said most probable disease by one (1) if the patient's physician confirms that the most probable disease is his or her actual disease.

* * * * *